US00PP31016P2

(12) United States Plant Patent
Rouwette

(10) Patent No.: US PP31,016 P2
(45) Date of Patent: Nov. 5, 2019

(54) ***HYDRANGEA* PLANT NAMED 'GRHYAR1407'**

(50) Latin Name: *Hydrangea arborescens*
Varietal Denomination: GRHYAR1407

(71) Applicant: Guido Rouwette, Valkenburg (NL)

(72) Inventor: Guido Rouwette, Valkenburg (NL)

( * ) Notice: Subject to any disclaimer, the term of this patent is extended or adjusted under 35 U.S.C. 154(b) by 0 days.

(21) Appl. No.: 16/350,320

(22) Filed: Nov. 1, 2018

(30) Foreign Application Priority Data

Aug. 10, 2018 (QZ) ..... PBR 20182082

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Annette H Para
(74) *Attorney, Agent, or Firm* — Penny J. Aguirre

(57) ABSTRACT

A new cultivar of *Hydrangea arborescens* plant named 'GRHYAR1407' that is characterized by its sturdy stems, its foliage that is bronze-green in color, and its large inflorescences that are pink in color.

2 Drawing Sheets

Botanical classification: *Hydrangea arborescens*.
Varietal denomination: 'GRHYAR1407'.

CROSS REFERENCE TO A RELATED APPLICATION

This application is co-pending with a U.S. Plant Patent Application filed for a plant derived from the same breeding program that is entitled *Hydrangea* Plant Named 'GRHYAR1406' (U.S. Plant patent application Ser. No. 16/350,319).

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1).

BACKGROUND OF THE INVENTION

The present invention relates to a new and distinct cultivar of *Hydrangea arborescens* and will be referred to hereafter by its cultivar name, 'GRHYAR1407'. 'GRHYAR1407' represents a new smooth *hydrangea*, a perennial shrub grown for landscape use.

'GRHYAR1407' derived from an ongoing breeding program by the Inventor in Valkenburg, The Netherlands. 'GRHYAR1407' arose as a controlled cross between an unnamed proprietary plant of *Hydrangea arborescens* from the Inventor's breeding program and *Hydrangea arborescens* 'Annabelle' (not patented) as the male parent in 2011. 'GRHYAR1407' was selected a single unique plant from amongst the resulting seedlings in summer of 2014.

Asexual propagation of the new cultivar was first accomplished by stem cuttings by the Inventor in summer of 2014 in Valkenburg, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'GRHYAR1407' as a unique cultivar of *Hydrangea arborescens*.

1. 'GRHYAR1407' exhibits sturdy stems.
2. 'GRHYAR1407' exhibits foliage that is bronze-green in color.
3. 'GRHYAR1407' exhibits large inflorescences that are pink in color.

The female parent of 'GRHYAR1407' differs from 'GRHYAR1407' in green foliage. The male parent of 'GRHYAR1407', 'Annabelle', differs from 'GRHYAR1407' in having white flowers and weaker stems. 'GRHYAR1407' can also be most compared to *Hydrangea arborescens* cultivars 'Abetwo' (U.S. Plant Pat. No. 20,571), 'NCHA1' (U.S. Plant Pat. No. 20,765) and 'GRHYAR1406', 'Abetwo' is similar to 'GRHYAR1407' in having strong stems. 'Abetwo' differs from 'GRHYAR1407' in having inflorescences that are white in color. 'NCHA1' is similar to 'GRHYAR1407' in having pink inflorescences. 'NCHA1' differs from 'GRHYAR1407' in having sterile flower sepals that are smaller in size and more rose in color and in having green foliage. 'GRHYAR1406' is similar to 'GRHYAR1407' in having pink inflorescences. 'GRHYAR1406' differs from 'GRHYAR1407' in having lighter pink inflorescences, a smaller plant size and foliage that is green in color.

BRIEF DESCRIPTION OF THE DRAWINGS

The accompanying colored photographs illustrate the overall appearance and distinct characteristics of the new *Hydrangea*. The photographs were taken of a plant three years in age as grown outdoors in a 10-liter container in Valkenburg, The Netherlands.

The photograph in FIG. 1 provides a view of a fully open inflorescence of 'GRHYAR1407'.

Figure 1:
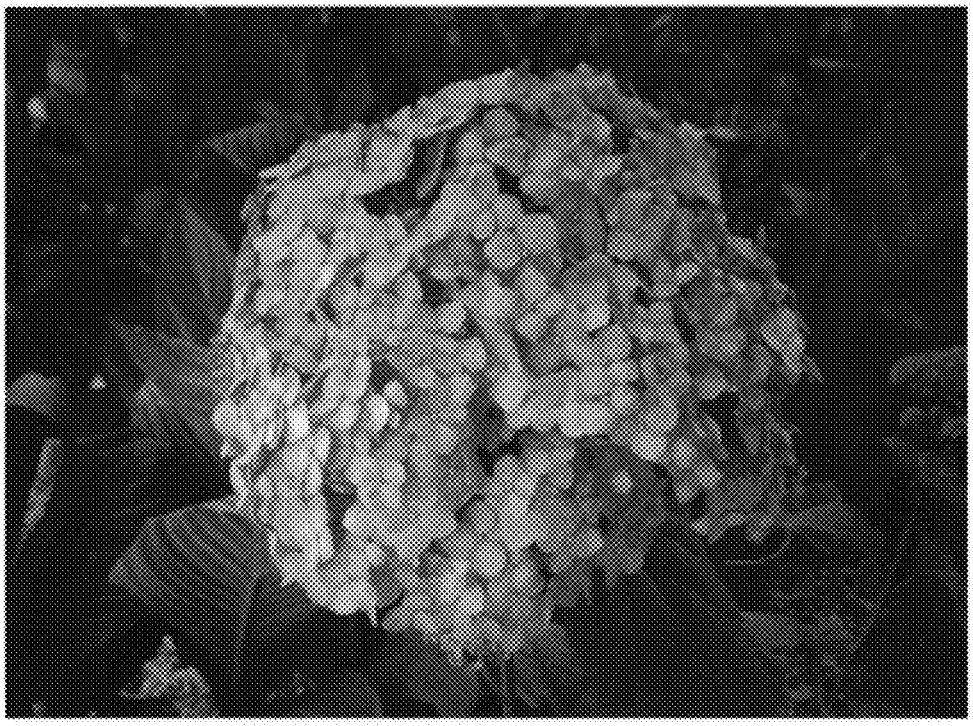
Figure 2:
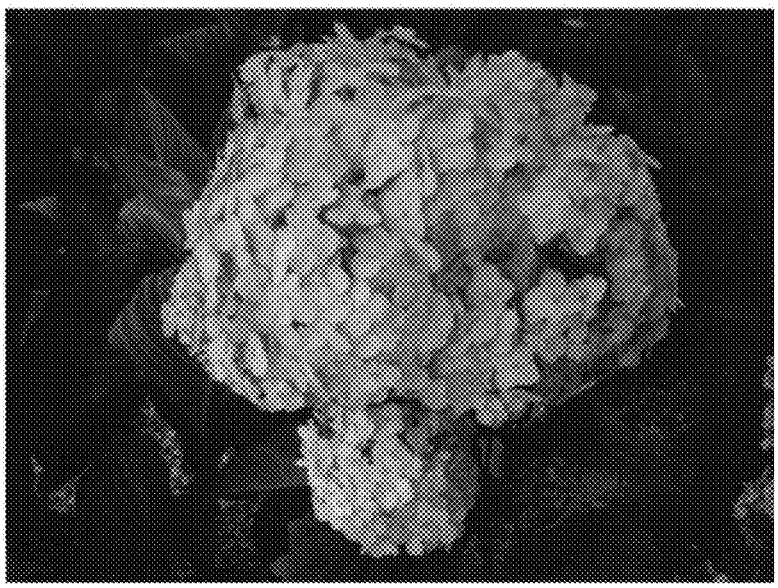

The photograph in FIG. 2 provides a view of a fading inflorescence of 'GRHYAR1407'.

Figure 3:
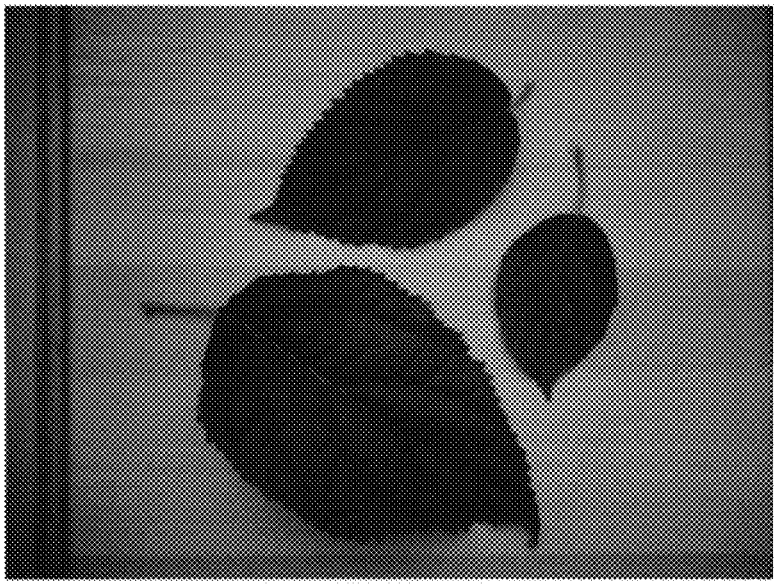

The photograph in FIG. 3 provides a close-up view of the leaves of 'GRHYAR1407'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of plants three years in age as grown outdoors in 10-liter containers in Valkenburg, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—From July to September in The Netherlands.

*Plant type*.—Perennial shrub with mophead-like corymbs.

*Plant habit*.—Sturdy stems, broadly obovate in shape.

*Height and spread*.—Reaches 1.2 to 1.5 m in height and 1 m in spread as a 3-year-old plant in the landscape.

*Cold hardiness*.—At least to U.S.D.A. Zones 5b.

*Diseases and pests*.—No susceptibility and resistance to pests and diseases has been observed.

*Root description*.—Fibrous and N155D and changing to 16D.

*Time required for root development*.—6 to 8 weeks for root initiation with a plant finished in a P9 container in about 12 months from a rooted cutting.

*Growth rate*.—Vigorous.

Stem description:

*Stem shape*.—Round.

*Stem color*.—New growth; 144C and flushed 59A, mature wood and bark; 164C and flushed 164A.

*Stem size*.—60 to 100 cm in length and 4 to 8 mm in diameter.

*Stem surface*.—Rugose with a few hairs when young and becoming glabrous when mature, no lenticels present.

*Stem aspect*.—Average angle 60° to 90° (soil level=0°).

*Internode length*.—6 to 17 cm.

*Branching*.—Average of 10 to 15 branches from base after 1 hard prune.

*Stem strength*.—Strong.

Foliage description:

*Leaf shape*.—Elliptic.

*Leaf division*.—Simple.

*Leaf size*.—Up to 20 cm in length and 10 cm in width.

*Leaf base*.—Obtuse.

*Leaf apex*.—Acuminate.

*Leaf venation*.—Pinnate, upper surface recessed and 145D in color, lower leaves raised and 144C in color.

*Leaf margins*.—Coarsely serrate.

*Leaf attachment*.—Petiolate.

*Leaf arrangement*.—Opposite.

*Leaf surface*.—Upper surface; glabrous with a few short hairs on main veins, lower surface; short hairy and more dense on veins.

*Leaf color*.—Immature leaves upper surface; 144A, immature leaves lower surface; 145B, mature leaves upper surface; NN137B with tinges and occasional spots of N77A, mature leaves lower surface; 143C.

*Petioles*.—Up to 5.5 cm in length and 3 to 5 mm in diameter, upper surface; somewhat canaliculated and short hairy and 164C in color and flushed with 164A, lower surface; glabrous and 164C in color.

Inflorescence description:

*Inflorescence type*.—Terminal mop-head; cymose corymb, comprised of showy flowers and fertile flowers.

*Lastingness of inflorescence*.—Up to 8 weeks.

*Inflorescence number*.—One per stem.

*Inflorescence size*.—Average of 18 cm in height and 30 cm in diameter.

*Inflorescence bracts*.—An average of 3, up to 2.1 cm in length and 6 mm in width, elliptic in shape, apex acuminate, base cuneate, margin entire, surface slightly arachnoid, 143C in color, occasionally present on fertile flower; filiform in shape and 1.5 mm in length, other characteristics similar to inflorescence bracts.

*Flower fragrance*.—No fragrance.

*Flower buds*.—Showy flowers; an average of 1.5 mm in length and 1 mm in diameter, ovate in shape, 60B in color, glabrous surface, fertile flowers; an average of 1.3 mm in length and 1.5 mm in diameter, broadly ovate in shape, 65A in color, glabrous surface.

*Showy flowers*.—800 to 1,200 per inflorescence, rotate. held outward, 3 mm in depth, 8 mm to 2.6 cm in diameter, last 6 to 8 weeks, persistent.

*Fertile flowers*.—An average of 200 to 300 per inflorescence, open campanulate in shape, held upright, 2 mm in depth, 3 mm in diameter, last about 3 days, self-cleaning.

*Peduncles*.—Strong, 1 to 5 cm in length and 1 to 3 mm in width, 139D in color and flushed with 59A, surface dense short hairy.

*Pedicels*.—Showy flowers; 8 mm to 1.3 cm in length, 8 mm in width, held at an angle between 30° to 90°, strong, 145C in color, surface short hairy, fertile flowers; 2 to 4 mm in length, 0.5 mm in width, typically held upright, moderately strong, 145C in color, surface short hairy.

*Petals*.—Showy flowers; 2 to 3, whorl arrangement, cymbiform in shape, entire margin, acute apex with obtuse tip, obtuse base, average of 1 mm in length and width, upper and lower surface glabrous, color; upper surface 63C, lower surface 69D, quickly fleeting, fertile flowers; 5, rotate in arrangement, triangular in shape, an average of 1 mm in length and width, acute apex, truncate base, entire margins, upper and lower surface glabrous, color; upper surface 149D, lower surface 149D flushed with 59A, quickly fleeting.

*Sepals*.—Showy flowers; typically 4 (occasionally 3 or 5), rotate in arrangement, broadly ovate-orbicular in shape, entire margin, broadly acute apex, obtuse base, up to 1.2 cm in length and 1.5 cm in width, upper surface glabrous with a few hairs at base, lower surface glabrous, color; upper surface when opening 62C with apex 60C, lower surface 62B and 62C, fully open upper surface; 69D with margin 69A and veins 69D, upper and lower surface fading; 141D with margins 142D, fertile flowers; 5, rotate in arrangement, elliptic in shape, acute apex, cuneate base, entire margin, an average of 2 mm in length and 1.5 cm in width, both surfaces glabrous and matte, color; upper and lower surface when opening and fully open 158D, quickly fleeting.

Reproductive organs:

*Presence*.—Both showy and fertile flowers are perfect.

*Stamens*.—Showy flowers; 6 to 7, filament is 2 to 4 mm in length, 155D in color with glabrous surface, anther is orbicular in shape, 0.3 mm in length and 69D in color, pollen is very low in quantity and 69D in color, fertile flowers; 9 or 10, filament is 2 to 5 mm in length and NN155D in color, anther is orbicular in shape, 0.5 mm in length and 65C in color, pollen is very low in quantity and too little for color reading.

*Pistils*.—Showy flowers; 1, an average of 1 mm in length, stigma is club-shaped with emarginated apex, stigma, style, and ovary N155C in color, fertile flowers; 2, an average of 1 mm in length, stigma is round in shape, stigma, style, and ovary NN155C in color.

*Fruit and seed*.—No fruit or seed production has been observed to date.

It is claimed:

1. A new and distinct cultivar of *Hydrangea* plant named 'GRHYAR1407' substantially as herein illustrated and described.

* * * * *